US006238705B1

(12) United States Patent
Liu et al.

(10) Patent No.: US 6,238,705 B1
(45) Date of Patent: *May 29, 2001

(54) BIOERODIBLE POROUS COMPOSITIONS

(75) Inventors: Lin-Shu Liu; Michael Froix, both of Mountain View; Jorge Heller, Woodside; Steven Y. Ng, San Francisco, all of CA (US)

(73) Assignee: Advanced Poymer Systems, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,044

(22) Filed: May 5, 2000

Related U.S. Application Data

(63) Continuation of application No. 08/806,513, filed on Feb. 24, 1997, which is a continuation-in-part of application No. 08/508,031, filed on Jul. 28, 1995, now abandoned.

(51) Int. Cl.[7] ............... A61K 9/50; B32B 5/16; B01J 13/02

(52) U.S. Cl. ............ 424/501; 424/502; 264/4.33; 264/4.6; 428/402

(58) Field of Search ............ 424/501, 502; 264/4.33, 4.6; 428/402

(56) References Cited

U.S. PATENT DOCUMENTS

| 4,663,286 | 5/1987 | Tsang et al. | 435/178 |
|---|---|---|---|
| 4,690,682 | 9/1987 | Lim | 604/891 |
| 4,690,825 | 9/1987 | Won | 424/501 |
| 4,803,168 | 2/1989 | Jarvis, Jr. | 435/240.22 |
| 4,806,360 | 2/1989 | Leong et al. | 424/487 |
| 4,855,144 | 8/1989 | Leong et al. | 424/487 |
| 4,923,645 | 5/1990 | Tsang et al. | 264/4.3 |
| 5,116,747 | 5/1992 | Moo-Young et al. | 435/178 |
| 5,145,675 | 9/1992 | Won | 424/78.31 |
| 5,334,640 | 8/1994 | Desai et al. | 524/56 |
| 6,096,344 | * 8/2000 | Liu et al. | 424/501 |

FOREIGN PATENT DOCUMENTS 0 306 236 A2   3/1989   (EP).

OTHER PUBLICATIONS

M. Daly et al., "Chitosan–Alginate Complex Coacervate Capsules: . . . ", Biotech. Progress, 4(2), 76–81 (1988).

T. Hayashi, "Polymer Microspheres as Carriers of the Immobilized Enzymes", Makromol. Chem., Macromol. Symp., 70/71, 137–145 (1993).

Y. Kikuchi et al., "Permeability Control of Polyelectrolyte Complex Membrane . . . ", Bull. Chem. Soc. Jpn., 61, 2943–2947 (1988).

E. Kokofuta et al., "Use of Polyelectrolyte Complex–Stabilized Calcium Alginate Gel . . . ", Biotech. Bioeng., 32, 756–759 (1988).

S. Kyotani et al., "A Study of Embolizing Materials for Chemo–embolization Therapy . . . ", Chem. Pharm. Bull., 40(10), 2814–2816 (1992).

Y.P. Li et al., "Preparation of Chitosan Microspheres Containing Fluorouracil . . . ", S. T. P. Pharma Sci., 1(6), 363–368 (1991).

(List continued on next page.)

Primary Examiner—Carlos A. Azpuru
(74) Attorney, Agent, or Firm—Heller Ehrman White & McAuliffe LLP

(57) ABSTRACT

A composition for the sequestration and sustained delivery of an active ingredient in the form of porous particles, the composition comprising the product of the controlled dehydration of particles formed by the reaction of a polymeric anionic material with a polyvalent cation. The composition may be loaded with an active ingredient by soaking the particles in a solution of the active ingredient; and may then be dehydrated. They may then be soaked in a solution of a polymeric cationic material, to form particles providing the controlled release of the active ingredient.

12 Claims, 4 Drawing Sheets-

OTHER PUBLICATIONS

Y. Nishioka et al., "Preparation and Release Characteristics of Cisplatin Albumin Microspheres . . . ", *Chem. Pharm. Bull.*, 37(11), 3074–1077 (1989).

Y. Nishioka et al., "A Study of Embolizing Materials for Chemo–Embolization Therapy . . . ", *Chem. Pharm. Bull.*, 40(1), 267–268 (1992).

Y. Ohya et al., "Thermo–sensitive Release Behavior of 5–Fluorouracil from Chitosan–Gel . . . ", *J. Bioact. Comp. Polymers*, 7, 242–256 (1992).

T. Ouchi et al., "Release Behavior of 5–Fluorouracil from Chitosan–Gel Microspheres . . . ", [*Journal, volume, and date unknown*], 360–361.

T. Sakiyama et al., "Preparation of a Polyelectrolyte Complex Gel from Chitosan . . . ", *J. Appl. Poly. Sci.*, 50, 2021–2025 (1993).

L. Szosland et al., "Production of Biocide–Containing Polymer Microspheres . . . ", *Int. Poly. Sci. Tech.*, 20(6), T/87–T/93 (1993).

B.C. Thanoo et al., "Cross–linked Chitosan Microspheres . . . ", *J. Pharm. Pharmacol.*, 44, 283–286 (1992).

H. Tomida et al., "A Novel Method for the Preparation of Controlled–Release Theophylline . . . ", *Chem. Pharm. Bull.*, 42(4), 979–981 (1994).

T. Sato et al., "Porous Biodegradable Microspheres for Controlled Drug Delivery . . . ", *Pharm. Res.*, 5, 21–30 (1988).

A. Supersaxo et al., "Preformed Porous Microspheres for Controlled and Pulsed Release . . . ", *J. Control. Rel.*, 23, 157–164 (1993).

C. Yan et al., "Dependence of Ricin Toxoid Vaccine Efficacy . . . ", *Vaccine*, 13, 645–651 (1995).

T.L. Bowersock et al., "Oral Vaccination with Alginate Microsphere Systems", *J. Control. Rel.*, 39, 209–220 (1996).

E.C. Downs et al., "Calcium Alginate Beads as a Slow–Release System . . . ", *J. Cell. Physiology*, 152, 422–429 (1992).

M.A. Wheatley et al., "Coated Alginate Microspheres: . . . ", *J. Appl. Poly. Sci.*, 43, 2123–2125 (1991).

L.–S. Liu et al., "Controlled Release of Interleukin–2 . . . ", *J. Control. Rel.*, 43, 65–74 (1997).

J. Heller et al., "Alginate/Chitosan Microporous Microspheres for the Controlled Release of Proteins and Antigens", *Pro. Intern. Symp. Control. Rel. Bioact. Mater.*, 23, (#351), 269–270 (1996).

\* cited by examiner

FIG. 6

BIOERODIBLE POROUS COMPOSITIONS

CROSS-REFERENCE TO RELATED APPLICATIONS

This application is a continuation of our application Ser. No. 08/806,513, filed Feb. 24, 1997. application Ser. No. 08/806,513 is a continuation-in-part of our then application Ser. No. 08/508,031, filed Jul. 28, 1995, now abandoned. These applications are incorporated herein by reference in their entirety.

BACKGROUND OF THE INVENTION

1. Field of the Invention

This invention relates to bioerodible porous compositions for the sequestration and sustained delivery of active agents, particularly pharmaceutical active agents.

2. Background to the Invention

Successful treatment of a variety of conditions is limited by the fact that agents known to effectively treat these conditions may have severe side effects, requiring low dosages to minimize these side effects. In other instances, the therapeutic agents may be very labile, or have very short half-lives requiring repeated administration. In still other instances, the long term administration of a pharmaceutical agent may be desired.

In all these cases, the ability to deliver a controlled dosage in a sustained fashion over a period of time may provide a solution. One method of doing so that has received a fair amount of attention is the sequestration and subsequent controlled release of active agents into and from porous compositions.

A number of publications describe the use of nondegradable porous microbeads. For example, U.S. Pat. No. 4,690,825 to Won describes delivery vehicles comprised of a polymeric bead, preferably made of polystyrene, or poly (methyl methacrylate) having a rigid, substantially non-collapsible network of pores with an active ingredient held within the network, for use in a method to provide controlled release of the active ingredient. The delivery vehicles can be polymerized by a process in which the active ingredient also comprises the porogen during formation of the network of pores. The beads may be dried to obtain a powder-like substance comprised of beads which retain the porogen within the network of pores. U.S. Pat. No. 5,145,675 to Won describes the use of a porogen in the preparation of polymer beads preferably made of polystyrene, or poly(methyl methacrylate) having a rigid, substantially non-collapsible network of pores. Active agents are then diffused into the porous beads from an external solution. However, both of these compositions are nondegradable and are thus only useful in topical applications where removal is not necessary. Clearly, for systemic applications where porous microparticles are implanted in an appropriate body site it is essential that the polymer microspheres be biodegradable.

Heretofore, major activity in the development of biodegradable microspheres has been concentrated on porous microspheres constructed from lactide/glycolide copolymers as described by Sato et al.(1988), *Pharm. Res.* 5: 21–30, or by Supersaxo et al. (1993), *J. Controlled Release* 23, 157–164. However, the preparation of these hollow microspheres requires the use of organic solvents such as methylene chloride which must be subsequently removed so that only a few parts per million remain, a very difficult task. Also, the bioerosion of lactide/glycolide copolymers is relatively slow. Further, even though lactide/glycolide copolymers have obtained FDA approval for certain uses, they are not GRAS ("generally regarded as safe") materials and for this reason, extensive toxicological studies are necessary before new uses are approved.

Thus, there exists a need to develop bioerodible, porous compositions that can be prepared in an aqueous environment, into which sensitive therapeutic agents can be easily and reproducibly incorporated and from which they can be released in an active state. It is further desirable that the materials used to make the compositions be GRAS ("generally regarded as safe") materials. Although there has been no reported work dealing with preparation of porous microspheres that can be prepared in an aqueous environment, there has been a great deal of work on solid porous particles that can be prepared in an aqueous environment. That work can be generally divided into work dealing with the incorporation of living cells, and work dealing with the incorporation of antigens and proteins.

U.S. Pat. No. 5,116,747 to Moo-Young et al. describes the immobilization of cells and other biologically active materials within a semipermeable membrane or microcapsule composed of an anionic polymer such as alginate induced to gel in the presence of calcium and/or a polymeric polycation such as chitosan. U.S. Pat. No. 4,663,286 to Tsang et al. describes the encapsulation of solid core materials such as cells within a semipermeable membrane, by suspending the core material in a solution of a water-soluble polyanionic polymer, preferably alginate salts, forming droplets, and gelling the polyanion with a polyvalent polycation such as a polypeptide, a protein or a polyaminated polysaccharide, preferably polylysine, polyarginine, or polyornithine. This patent further teaches controlling the porosity and permeability of the disclosed compositions to molecules ranging from about 60,000 to about 900,000 Daltons by changing the degree of hydration of the polymer. Incubation in saline or chelating agents increases hydration and expands the gels, whereas incubation in calcium chloride contracts the gel mass. Increases in charge density of the polycationic membrane generally produces smaller pores. Increases in the molecular weight of the polycationic polymer generally produce a thicker, less permeable membrane. U.S. Pat. No. 4,803,168 to Jarvis describes the encapsulation of core materials such as cells, enzymes, antibodies, hormones, etc. within a semipermeable membrane or microcapsule composed of an aminated polymeric inner layer such as chitosan ionically bound to an anionic polymeric outer layer such as polyglutamic or polyaspartic acid, and having a porosity of about 80,000 Daltons.

A number of publications describe the incorporation of antigens and proteins into calcium alginate microparticles. For example, Bowersock et. al. (1996), *J. Controlled Release* 39: 209–220, describe development of oral vaccines using an alginate microsphere system and Downs et. al. (1992), *J. Cell. Physiol.* 152: 422–429 describe the release of growth factors from calcium alginate beads. However, entrapment efficiency was very low and typically, more than 90% of the active agent is not incorporated. Because many of these agents are very expensive, and in some cases high concentration of the active agent in the microsphere is desired, improved methods for preparing drug-loaded microspheres are needed.

A publication by Wheatley et. al. (1991), *J Appl. Polymer Sci.*, 43: 2123–2135, describes a method for improving entrapment efficiency in alginate/polycation microspheres. In this method a diffusion-filling technique is used where blank calcium alginate beads are coated twice with small amounts of a polycation and protein then loaded into these capsules by stepwise diffusion from solutions of increasing drug concentration. This is then followed by a final coating with a polycation. This is a laborious and timeconsuming process that requires a number of steps, i.e. empty alginate bead formation, precoating with a polycation, multistep diffusion of drug into the bead and final coating with a polycation. Even using this complex procedure, a maximal loading of only 30 wt. % could be achieved.

The disclosures of these and other publications referred to throughout this application are incorporated herein by reference.

BRIEF SUMMARY OF THE INVENTION

We have now discovered that if we prepare porous particles of a composition (such as calcium alginate microspheres) by dispersing a solution of a polymeric anionic material (such as sodium alginate or other polysaccharides bearing carboxyl functionalities) into a solution of a polycation (such as calcium chloride solution) and then dehydrate the particles by controlled dehydration (e.g. lyophilization), a highly porous bioerodible particle forms into which therapeutic agents can be diffused from an external solution. Once the diffusion process has been completed, the particles may again be dehydrated by controlled dehydration, and then coated with a polycation. We have further discovered, that the amount of polycation used to coat the particles can control the release of an incorporated active ingredient within unexpectedly wide limits. In this way, crosslinked, polycation coated particles having a drug loading in excess of 50 wt. % and that can release drugs in a controlled manner have been achieved.

It is an objective of this invention to provide porous bioerodible compositions for the sequestration and sustained delivery of active ingredients, which compositions are well tolerated by mammals and enable the sequestration and delivery of a greater amount of the active ingredient than prior art compositions. Accordingly, the invention provides macroporous compositions of ionically cross-linked polyanions and polycations into which more than 50 wt. % of a water-soluble active agent can be incorporated and from which it can be released in a controlled manner.

Active agents can be introduced subsequently by diffusing the active agent into the porous compositions from an external aqueous solution. Because the active agent is never exposed to harsh experimental conditions or to organic solvents, biological activity is retained.

A preferred embodiment comprises macroporous bioerodible particles prepared from alginate and chitosan, which have been ionically crosslinked and thus have not undergone any changes that would alter their GRAS status. Although a number of experimental procedures can be utilized to prepare the compositions of the invention, a particularly advantageous method uses calcium alginate particles having a preselected size and size distribution which have been created by spraying sodium alginate into a calcium chloride solution and then lyophilizing to create a porous structure, stirring in a drug solution and then incubating in a chitosan solution.

BRIEF DESCRIPTION OF THE DRAWINGS

FIG. 6 illustrates the immunogenicity of ricin toxoid vaccine sequestered within alginate/chitosan microspheres.

DETAILED DESCRIPTION OF THE PREFERRED EMBODIMENTS

Figure 1A:
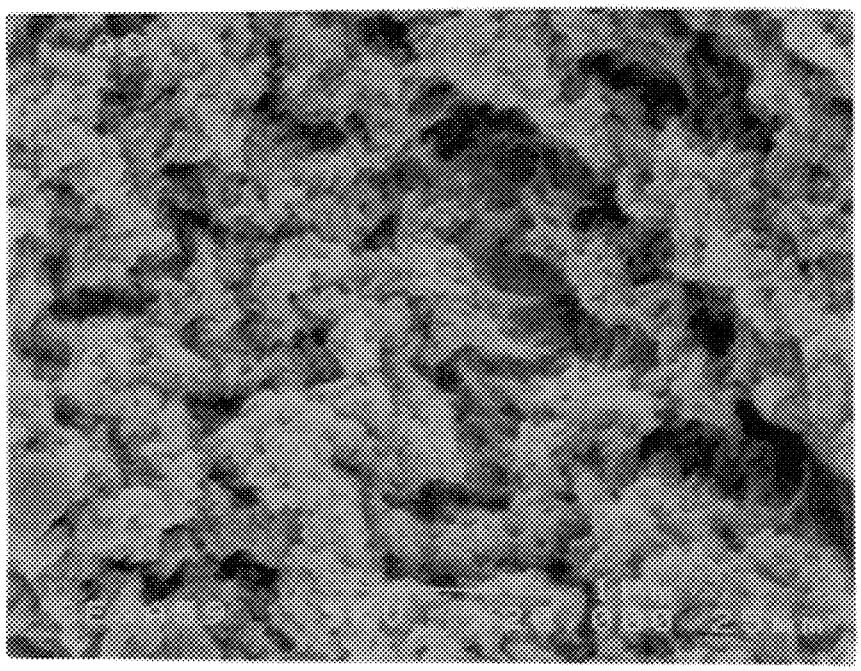
FIG. 1A is a scanning electron micrograph (SEM) of the surfaces of alginate/chitosan microspheres (particles according to this invention)

In the instant invention, a porous delivery vehicle comprised of a polymeric composition having an active ingredient held within the pores is utilized to provide a controlled time release of the active ingredient. In accordance with the present invention, the active ingredient is released from the porous delivery vehicle in a sustained fashion.

One property of the compositions provided herein that distinguish them from all prior art is their greatly enhanced ability to absorb drugs and the prolonged release possible. The prior art neither teaches nor suggests macroporous polyelectrolyte compositions of the type disclosed herein prepared by controlled dehydration, nor discloses prolonged release or readily controllable kinetics.

DEFINITIONS

"Porous matrix" denotes the physical structure of the composition formed as a result of the electrostatic ionic interaction between a first polymeric ion with a multifunctional cation and a third multivalent or polymeric ion having an opposite charge. When such a first and second and third polymeric or polyvalent ions having opposite charges are contacted in a solution, they often form spherical polyelectrolyte particles, termed microspheres or beads, which may range in size from less than 1 to about 1000 μm. However, other shapes, such as irregularly shaped particles, or larger compositions readily visible to the naked eye, are also contemplated.

"Bioerodible" signifies that the porous matrix may be disassembled or digested into its component molecules by the action of the environment or particularly by the action by living organisms, and optionally metabolized or digested into simpler constituents without poisoning or distressing the environment or the organism. Bioerodible compositions according to the invention are preferably made of GRAS materials. Preferred polyelectrolyte combinations are alginate/chitosan, alginate/polylysine, alginate/polyarginine, gum arabic/albumen, galactan sulfate/chitosan, alginate/polyvalent cations (e.g., calcium), polyphosphagine/polyvalent cations, but other materials and combinations are possible that are within the knowledge of persons of ordinary skill. The concentration of the polymeric anionic molecule and the polymeric cationic molecule used to formulate the composition independently ranges from about 0.1 to about 15% w/v. Preferably, the concentration of the polymeric anionic molecule and the polymeric cationic molecule used to formulate the composition independently ranges from about 0.5 to about 5% w/v. Most preferably, the concentration of the polymeric anionic molecule and the polymeric cationic molecule used to formulate the composition independently ranges from about 0.5 to about 3% w/v. Different proportions of polycations and polyanions may be used, depending on the nature of the active ingredient, the desired pore size, the desired capacity to uptake water and/or the desired rate of releasing the active ingredient.

"Alginate" or "algin" denotes the sodium salt of alginic acid (polymannuronic acid). Alginate is a gelling polysaccharide, typically extracted from kelp; and is the sodium salt of a linear polymer of $\beta$-(1→4)-D-mannosyluronic acid and $\alpha$-(1→4)-D-gulosyluronic acid residues, the proportions of which vary with the source and state of maturation of the plant.

"Chitosan" is the deacylated form of chitin, and is a cellulose-like biopolymer consisting predominantly of unbranched chains of $\beta$-(1→4)-2-amino-2-deoxy-D-glucose (also known as D-glucosamine) residues.

"Macroporous" denotes a composition comprised of a network of interconnected pores whose capacity to absorb and retain drugs has been enhanced in comparison with composition lacking a network of interconnected pores. A preferred method for forming such a network of interconnected pores is by controlled dehydration.

"Controlled dehydration" denotes methods for dehydration which avoid collapsing the porous network and/or maintain or enhance the macroporous matrix and fluid uptake. The preferred method of controlled dehydration for the compositions of this invention is lyophilization, also known as freeze drying, but other methods may be used, such as exposure to a graded series of solvents (e.g., alcohols) that extract the water without collapsing the structure of the polyelectrolyte matrix.

"Sequestration" denotes that an active ingredient is reversibly confined or held within the porous spaces of the porous matrix. The active ingredient may be a freely diffusible solute in a fluid medium that fills the pore, but the term sequestration also encompasses active ingredients in the solid or gaseous state, or an interaction between the matrix and the active ingredient, such as an electrostatic attraction or a hydrophobic interaction, that reversibly attaches the active ingredient to the matrix.

An "active ingredient" is any functional ingredient or ingredient which is released from the porous matrix to perform some function. "Active ingredient" is broadly defined to encompass any functional ingredient so long as it is held within the network of pores of a porous composition according to the present invention. Thus, for example, the active ingredient might comprise anti-infectives (such as antibiotics, fungicides, scabicides, pediculicides or miscellaneous anti-infectives such as iodine), anti-inflammatory agents, antipruritics, astringents, anti-hidrotics, keratolytic agents and caustics, keratoplastic agents, rubefacients, sunscreens, pigmentation agents, emollients, demulcents, protectants and detergents. The active ingredient might be used in a variety of applications such as beauty aids, including cosmetic and toiletry applications, and the active ingredient may be incorporated in a medium such as a gel, a cream, a lotion, an ointment, a liquid or the like. The active ingredient may be a living cell, a vaccine, a growth factor, a protein or peptide drug (.e.g. insulin, erythropoietin), a vitamin (e.g., vitamin B-12).

"Administered to a mammal" means that the composition containing an active ingredient is administered orally, parenterally, enterically, gastrically, topically, transdermally, subcutaneously, locally or systemically. The composition may optionally be administered together with a suitable pharmaceutical excipient, which may be a saline solution, ethyl cellulose, cellulose acetatephtalates, mannitol, lactose, starch, magnesium stearate, sodium saccharin, talcum, glucose, sucrose, carbonate, and the like.

"Sustained delivery" or "sustained time release" denotes that the active ingredient is released from the delivery vehicle at an ascertainable and manipulatable rate over a period of minutes, hours, days, weeks or months, ranging from about thirty minutes to about two months. The release rate may vary as a function of a multiplicity of factors such as particle size, particle composition, particle hydration, pore size, solvent composition, solubility of the active ingredient and molecular weight and charge density of the active ingredient.

Sequestration of an active ingredient within the pores of a porous delivery vehicle may serve one or more purposes. It may limit the toxic effect of a compound, prolong the time of action of a compound in a controlled manner, permit the release of an active ingredient in a precisely defined location in an organism, protect unstable compounds against the action of the environment, convert a liquid or gaseous substance into a pseudosolid material, or mask an unpleasant odor or taste.

To utilize a delivery vehicle in accordance with the method of the present invention, the delivery vehicle is mixed with a medium to form a mixture which is applied to a surface or administered to a mammal. The active ingredient is then released from the network of pores by diffusion or volatilization. Alternatively, the active ingredient may be released by a force such as pressure. Pressure release may by gradual and continuous. Pressure release may also be triggered by intermittent pressure which may vary the concentration of active ingredient released from the network of pores.

The delivery vehicle may be incorporated in a medium, such as a solution, suspension, tablet, pill, capsule, powder, gel, cream, lotion, ointment, liquid, aerosol or the like, which may then be applied to a surface, injected, is inhaled, or administered to a mammal orally or parenterally. For example, the delivery vehicle containing the active ingredient might be incorporated into cosmetic preparations such as hand creams, acne products, deodorants, antiperspirants, baby powders, foot powders, body powders, lip ices, lip sticks, baby creams and lotions, mouthwashes, dentifrices, medicated facial creams and lotions, shampoos, shaving creams, pre- and after-shave lotions, depilatories and hair grooming preparations. The active ingredient may then be released by pressure, diffusion or volatilization. Thus, the delivery vehicle is uniquely suited for use in a wide variety of applications in which it is desirable to release an active ingredient by one or more methods.

The invention is illustrated further in the following Examples.

EXAMPLE 1

Preparation of Protein-Loaded Porous Alginate/Chitosan Microspheres

Porous alginate beads were first formed by inducing the gelation of sodium alginate solution with $CaCl_2$ followed by lyophilization. Then, the desired protein was entrapped into the porous alginate/$CaCl_2$ beads by stirring the alginate beads in a protein solution having the desired concentration. Next, a calculated volume of chitosan solution was added to the alginate beads containing entrapped protein.

Figure 1B:
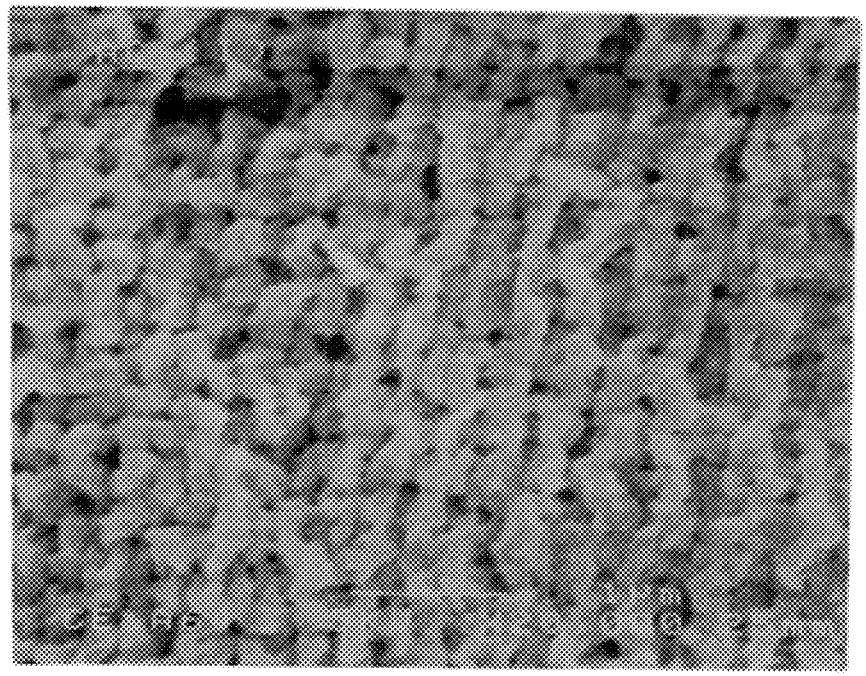
FIG. 1B is a SEM of the interiors.
Figure 2:
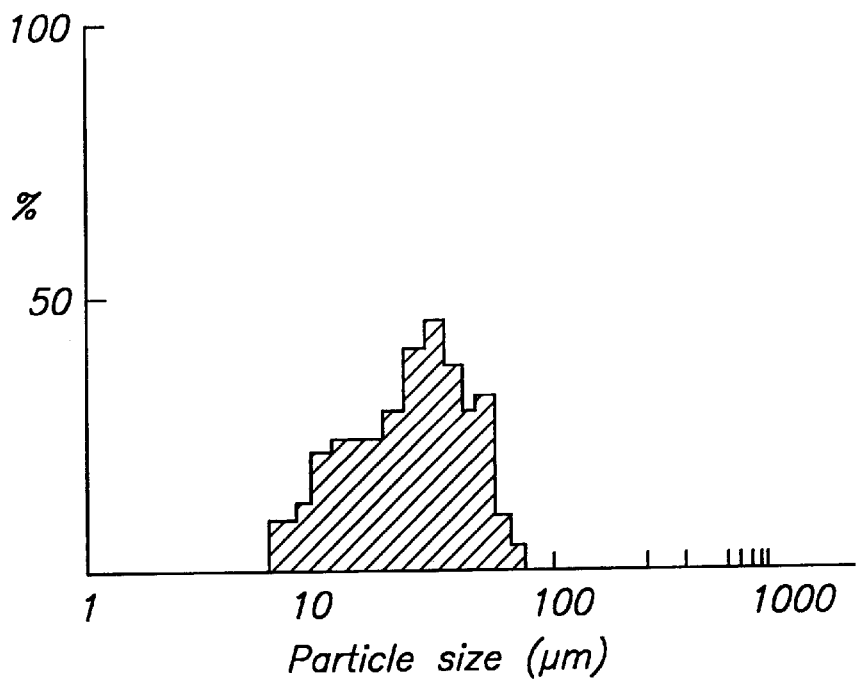
FIG. 2 illustrates the size distribution of alginate/chitosan microspheres.

Calcium chloride-crosslinked alginate beads were formed by infusing a 2–3% (w/v) sodium alginate solution at pH 6.5 into an atomizer at a rate of 1.91 mL/min using an automatic infusion/withdrawal pump (model 600–950; Harvard Apparatus Co., Dover, Mass., and sprayed, with the help of a nitrogen jet at 3–4 psi into 800 mL of a 0.5% $CaCl_2$ solution under magnetic stirring. The thus-formed beads were allowed to stand in the $CaCl_2$ solution for 10 min. to complete the cure. The $CaCl_2$ solution was decanted, and the resulting microspheres washed several times with deionized water and lyophilized to form the porous microspheres of this invention. FIG. 1A is a scanning electron micrograph (SEM) of the surface of a microsphere according to this invention; FIG. 1B is a similar SEM showing the interior of a microsphere. As may be seen from the SEMs, the microspheres show a fibrous macroporous structure. The pores form as a consequence of the controlled drying (lyophilization) process since during crosslinking the polysaccharides swell in a continuous liquid phase which is removed during lyophilization. FIG. 2 illustrates the size distribution of microspheres prepared according to this invention; 90% of the microspheres have diameters between 20 and 100 $\mu$m.

The resulting porous alginate beads were then stirred in a protein solution having the desired concentration for 30 min. at room temperature, thereby filling the pores of the beads with the protein, and dried. Then, chitosan dissolved in a minimum amount of phosphate buffered saline (PBS) was slowly added to the $CaCl_2$-crosslinked alginate microspheres containing entrapped protein, to encapsulate the protein in the microspheres, and the final product was obtained by lyophilization.

EXAMPLE 2

Sustained Release of Bovine Serum Albumin (BSA) from Alginate/Chitosan Microspheres FITC-BSA loaded microspheres were prepared by mixing PBS containing bovine serum albumin-fluorescein isothiocyanate (FITC-BSA) with alginate/chitosan microspheres prepared as in Example 1 containing various percentages of chitosan. BSA release from the microspheres was determined with a USP dissolution apparatus at 50 rpm, using 100 mL of PBS as dissolution medium, and 50 mg of microspheres loaded with FITC-BSA. The release of FITC-BSA was monitored by UV absorption at 495 nm.

Figure 3:
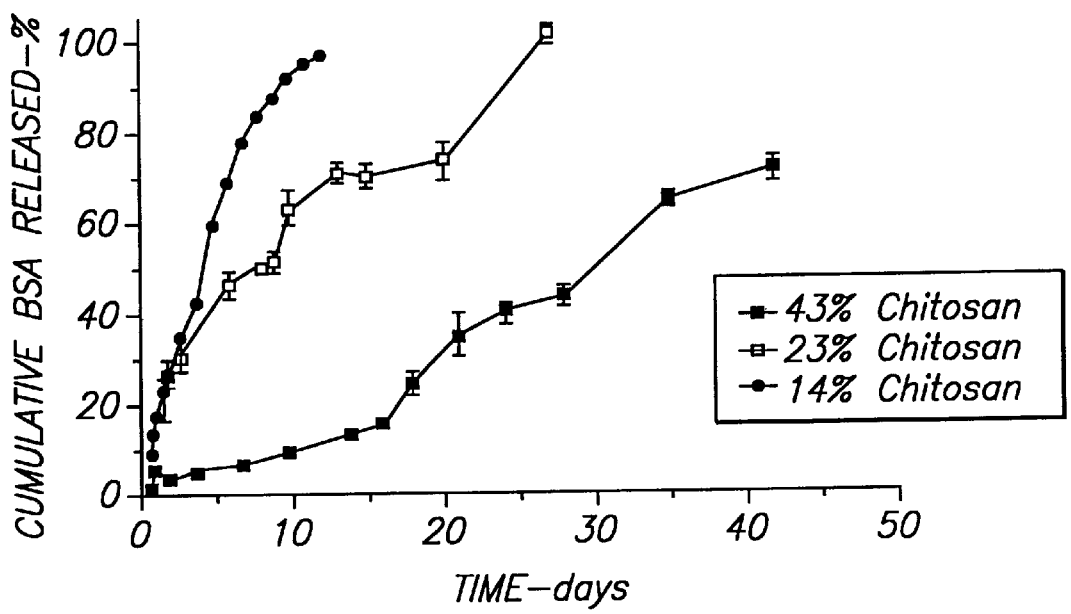
FIG. 3 illustrates the release of bovine serum albumin (BSA) sequestered within alginate/chitosan microspheres.

The results are shown in FIG. 3. It is clear that variation in the amount of chitosan used allows the preparation of particles that can release BSA at relatively constant kinetics for periods of time ranging from days to months.

EXAMPLE 3

Sequestration and Sustained Release of Interleukin-2 (IL-2), and Immunostimulation with IL-2-Containing Macroporous Microspheres.

Cytotoxic T-lymphocytes (CTL) have been widely investigated as effective killer cells for cancer clinical immunotherapy. CTL can be induced by co-culturing tumor cells and peripheral immune cells in the presence of interleukin. However, due to the short half-life of interleukin, inconvenient multiple injections are required. Further, to be effective, high doses of interleukin are required, which can result in side-effects, such as coma or dehydration.

One approach to overcome these obstacles is to use an appropriate controlled release system. Accordingly, chitosan/alginate particles containing sequestered IL-2 were synthesized essentially as described in Example 1. In this particular case, the porous particles (1 g) were incubated in an IL-2 (Riken Cell Bank, Japan) solution (4 mL, 1500 U/ml IL-2 in PBS) for 1 hr.

Interleukin-2 release was determined as follows: A 6-well cell culture plate equipped with a porous membrane insert (pore size, 0.45 nm), which separates the well into two levels was used. Macroporous particles loaded with IL-2 were placed on the top of the isolation membrane, and 5.0 mL of the culture medium [RPMI 1640 cell culture medium (Gibco BRL, Tokyo, Japan) containing 5% heat-inactivated fetal calf serum], and the amount of released IL-2 present in the lower chamber was determined by using an IL-2 ELISA kit.

Figure 4:
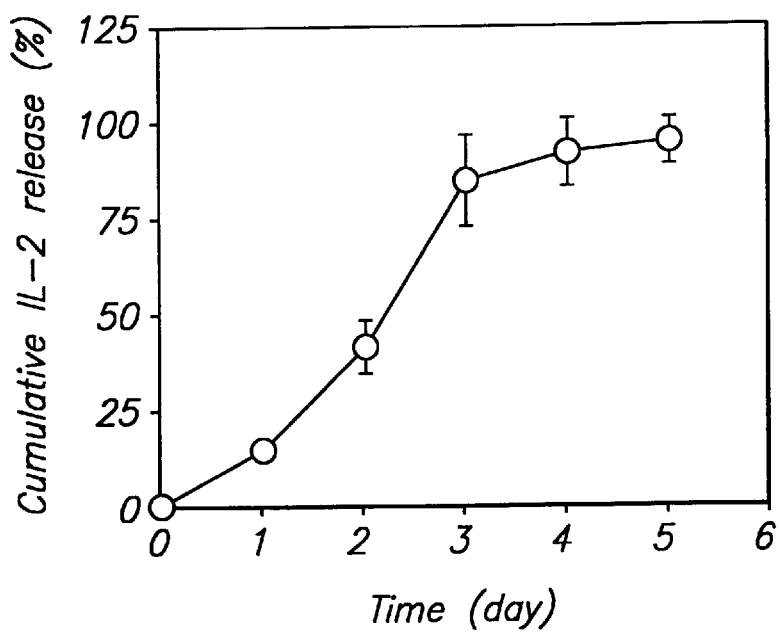
FIG. 4 illustrates the release of IL-2 sequestered within alginate/chitosan microspheres.

As shown in FIG. 4, the IL-2 release from the alginate/chitosan particles took place over 5 days, and almost 100% of the active IL-2 was recovered in the cell culture medium.

Induction of CTL: Human lung squamous cell carcinoma SQ-5 cells (SQ-5) (Riken Cell Bank, Kyoyadai, Japan), grown to a confluent state, and peripheral blood mononuclear monocytes (PBMC) (from volunteers), 5 mL at $1 \times 10^7$ cells/mL, were placed in the lower level of a 6-well multiplate equipped with a porous membrane (0.45 nm, pore size) to separate the well into two levels, and the alginate/chitosan/IL-2 (0.1 g; about 600 U/well) particles were loaded above the membrane. On-half the medium was changed each day. After one week in culture, induced lymphocytes were isolated from the mixture, and their tumor killing activity measured. As a control, an amount of free soluble IL-2 (about 250 U) was added to the plate daily for 5 days.

Tumor killing activity assay: Target tumor cells (SQ-5, AOI, and A549) were seeded into 96-well multiplate containing 100 $\mu$L of culture medium, and 100 $\mu$L of CTL with the desired effector/target ratios was added. After incubation for 24 hr. at 37° C., the cells were fixed with 10% formalin overnight, and then gently washed by immersing the plate into tap water. Cells on the bottom of the wells were stained with crystal violet (0.4% in PBS) for one hour, the dye extracted with ethanol, and the absorbance at 540 nm determined.

The same number of lymphocytes were induced by the daily addition of free IL-2, for a total of five doses, and by continuous exposure to a single dose of IL-2 sequestered within macroporous alginate/chitosan particles. Moreover, the CTL induced by alginate/chitosan/IL-2 macroporous particles attack and solubilize SQ-5 cells as specifically as those induced by soluble interleukin-2, indicating the feasibility of using controlled release of cytokines to regulate the immune system. The controlled delivery of L-2 is more efficient, both in terms of units of IL-2 expended and of the number of manipulations required.

EXAMPLE 4

Sequestration and Sustained Release of Ricin Toxoid Vaccine from Particles

Chitosan/alginate particles containing sequestered ricin toxoid vaccine were synthesized generally as described in Example 2, except that 0.3% ricin toxoid vaccine in PBS was used instead of FITC-BSA.

Alginate/chitosan particles containing 50 mg of ricin toxoid vaccine were placed in polypropylene tubes containing 10 mL of PBS and continuously agitated at 37° C. At selected time intervals, the solution was centrifuged and the supernatant fluid sampled and measured by an ELISA method.

Figure 5:
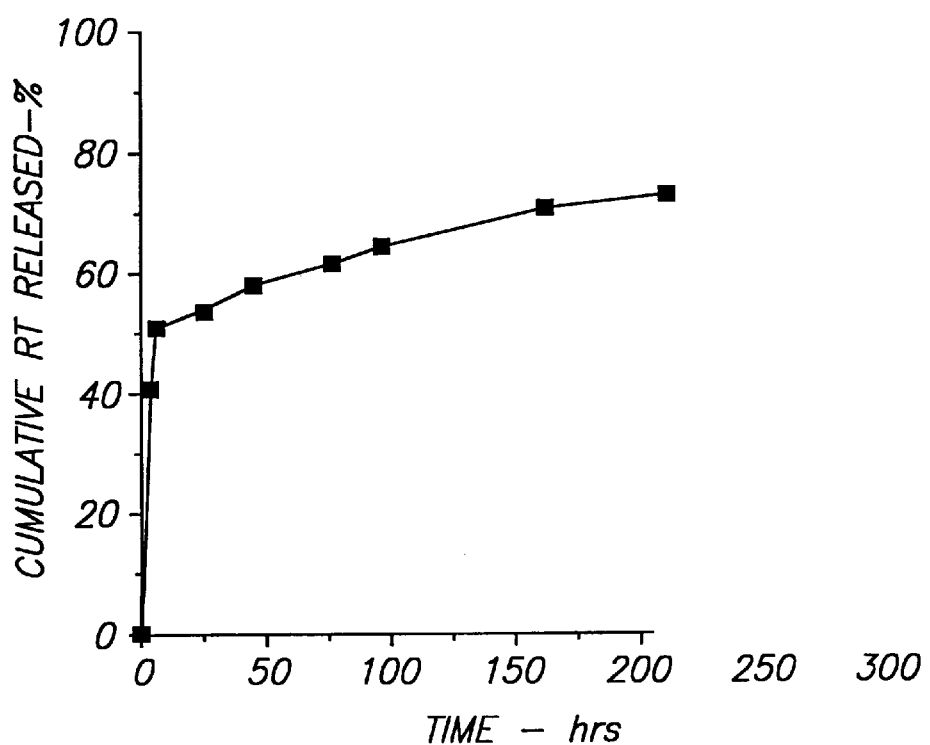
FIG. 5 illustrates the sustained release of ricin toxoid vaccine sequestered within alginate/chitosan microspheres.

As shown in FIG. 5, ricin toxoid vaccine release from the alginate/chitosan microspheres took place over 10 days.

EXAMPLE 5

Immunogenicity of Alginate/Chitosan Macroporous Particles Containing Ricin-Toxoid Vaccine The immunological activity of ricin toxoid vaccine loaded alginate/chitosan particles were evaluated essentially as described in Yan et al. (1995) *Vaccine* 13: 645. Healthy adult mice were housed in bioclean cages and fed and watered ad libitum prior to immunization. Vaccine-containing particles were subcutaneously administered as a single dose. Solution vaccine was subcutaneously administered to control mice. Six weeks later, the mice were exposed to ricin by means of an aerosol spray. The dose of ricin was 60 $\mu$g/kg via whole body exposure. The exposed mice were observed daily for 3–4 weeks, and vaccine efficacy was measured, with survival as the endpoint.

Figure 6:
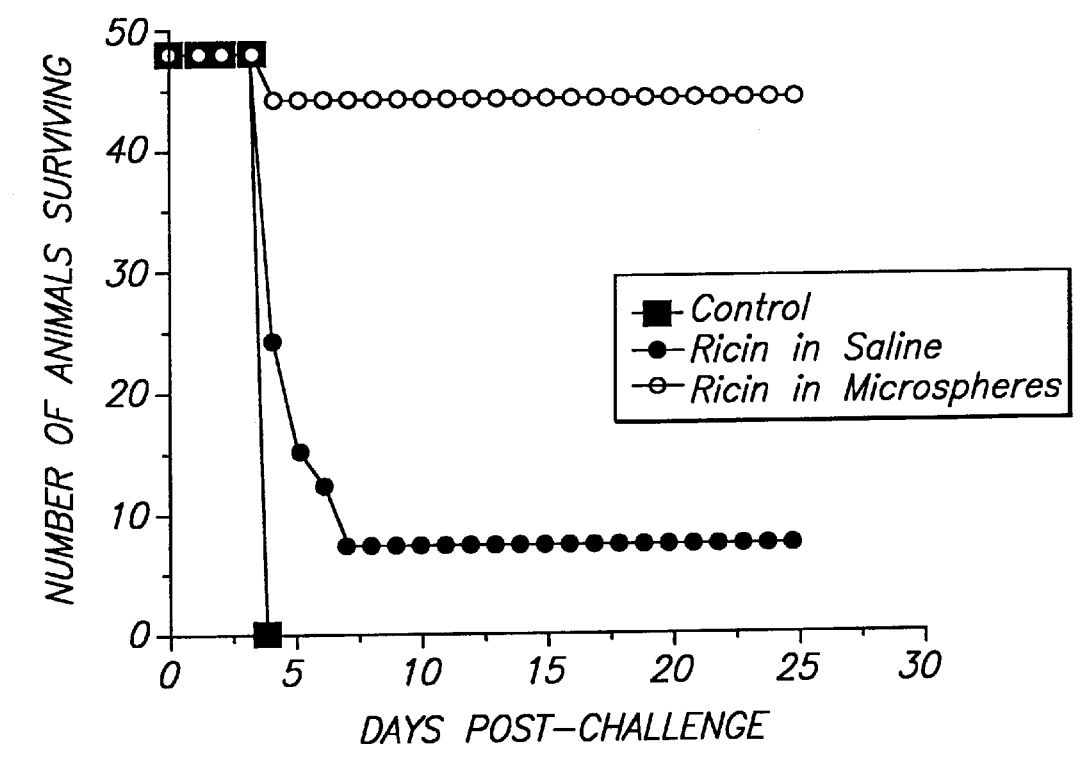

The results are shown in FIG. 6. All control nonimmunized mice died 4 days after exposure to ricin. Four weeks after exposure to ricin, 16% of mice immunized with solution vaccine survived, whereas 91% of mice immunized with vaccine sequestered in the porous microspheres of this invention survived. Clearly, immunization with chitosan/alginate particles containing ricin toxoid vaccine was significantly more efficient than immunization with soluble vaccine.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. A method of preparing a time-release delivery composition containing an active ingredient for the sustained delivery of that active ingredient, the method comprising:
   (a) forming a plurality of microspheres by the dispersion of droplets of a solution of a polymeric anionic material into a solution of a polyvalent cation;
   (b) dehydrating the microspheres by controlled dehydration;
   (c) loading the microspheres with the active ingredient by soaking the microspheres in a solution containing the active ingredient; and
   (d) drying the resulting loaded particles.

2. The method of claim 1 where the polymeric anionic material is selected from the group consisting of alginate, polyvinyl alcohol, galactan sulfate, polyacrylic acid, gum arabic, and polyphosphagine.

3. The method of claim 2 where the polymeric anionic material is alginate.

4. The method of claim 1 where the polyvalent cation is calcium ion.

5. The method of claim 1 where the active ingredient is a protein or peptide.

6. The method of claim 1 where the particles have a diameter from about 1 micron to 1000 microns.

7. A time-release delivery composition containing an active ingredient for the sustained delivery of that active ingredient, the composition comprising the product of the method of claim 1.

8. The composition of claim 7 where the polymeric anionic material is selected from the group consisting of alginate, polyvinyl alcohol, galactan sulfate, polyacrylic acid, gum arabic, and polyphosphagine.

9. The composition of claim 8 where the polymeric anionic material is alginate.

10. The composition of claim 7 where the polyvalent cation is calcium ion.

11. The composition of claim 7 where the active ingredient is a protein or a peptide.

12. The composition of claim 7 where the particles have a diameter from about 1 micron to about 1000 microns.

* * * * *